US011242566B2

(12) United States Patent
Glavey et al.

(10) Patent No.: US 11,242,566 B2
(45) Date of Patent: Feb. 8, 2022

(54) SIALYLTRANSFERASE ST3GAL6 AS A MARKER FOR MULTIPLE MYELOMA

(71) Applicant: NATIONAL UNIVERSITY OF IRELAND, GALWAY, Galway (IE)

(72) Inventors: Siobhan Glavey, Galway (IE); Lokesh Joshi, Galway (IE); Michael O'Dwyer, Galway (IE)

(73) Assignee: National University of Ireland, Galway, Galway (IE)

( * ) Notice: Subject to any disclaimer, the term of this patent is extended or adjusted under 35 U.S.C. 154(b) by 545 days.

(21) Appl. No.: 15/597,961

(22) Filed: May 17, 2017

(65) Prior Publication Data

US 2017/0327899 A1 Nov. 16, 2017

Related U.S. Application Data

(62) Division of application No. 14/435,001, filed as application No. PCT/EP2013/071555 on Oct. 15, 2013, now abandoned.

(30) Foreign Application Priority Data

Oct. 15, 2012 (EP) .................................... 12188596

(51) Int. Cl.
*A61K 31/7105* (2006.01)
*C12Q 1/6886* (2018.01)
*G01N 33/574* (2006.01)

(52) U.S. Cl.
CPC ........ *C12Q 1/6886* (2013.01); *A61K 31/7105* (2013.01); *G01N 33/57407* (2013.01); *G01N 33/57423* (2013.01); *C12Q 2600/106* (2013.01); *C12Q 2600/118* (2013.01); *C12Q 2600/158* (2013.01); *G01N 2333/91* (2013.01); *G01N 2333/91148* (2013.01); *G01N 2333/924* (2013.01); *G01N 2400/00* (2013.01)

(58) Field of Classification Search
CPC .................................................... C12Q 1/6886
USPC ......................................................... 435/7.23
See application file for complete search history.

(56) References Cited

U.S. PATENT DOCUMENTS

2008/0119443 A1* 5/2008 Li ............................... C07J 1/00
514/169
2009/0214439 A1* 8/2009 Kumar ..................... C07H 7/00
424/9.35

FOREIGN PATENT DOCUMENTS

EP 2236607 A1 10/2010
WO 01/68095 A1 9/2001

OTHER PUBLICATIONS

Azab et al (Blood, 2012, 119(6): 1468-1478).*
Azab et al (Blood, 2010, 116(21): Abstract453).*
Nishizawa et al (Nihon Kokyuki Gakkai Zasshi, 2005, 43(4): Abstract).*
Peet et al. (PLoS ONE, 2012, 7(2): 1-10).*
Dinser et al (Eur J Haematol, 2005, 74(5): Abstract).*
Frithz et al: "Serum sialyltransferase and fucosyltransferase activities in patients with multiple myeloma", European Journal of Cancer and Clinical Oncology, vol. 21, No. 8, 1985, pp. 913-917.
Yang et al: "Coordinated roles of ST3Gal-VI and ST3Gal-IV sailyltransferases in the synthesis of selectin ligands", Blood, vol. 120, No. 5, 2012, pp. 1015-1026.
Chiang et al. "A novel sialyltransferase inhibitor AL10 suppresses invasion and metastasis of lung cancer cells by inhibiting integrin-mediated signaling", Journal of Cellular Physiology, vol. 223, No. 2, 2010: pp. 492-499.
Laury-Kleintop et al: "Antibody-affinity purification of novel alpha-L-fucosidase from mouse liver", The Biochemical Journal, 1987, pp. 589-593.
Johnson et al: "Analysis of purified human liver x-L-fucosidase by Western-blotting with lectins and polyclonal and monoclonal antibodies", Biochem. J, 1992, pp. 829-834.
Lin et al: "Mutation identification and characterization of a Taiwanese patient with fucosidosis", Journal of Human Genetics, vol. 52, No. 6, 2007, pp. 553-556.
Marcos et al: "Polypeptide GalNAc-transferases, ST6GalNAc-transferase I, and ST3Gal-transferase I expression in gastric carcinoma cell lines", Journal of Histochemistry and Cytochemistry, vol. 51, No. 6, 2003, pp. 761-771.
Glavey et al: "Glycosylation-Related Gene Expression Is Dysregulated in Multiple Myeloma and Overexpression of the Sialyltransferase ST3GAL6 Is Associated with Inferior Survival", Blood, vol. 120, No. 21, 2012, p. 2931.
International Search Report and Written Opinion in PCT/EP2013/071555, dated Mar. 1, 2014.

* cited by examiner

Primary Examiner — Sean E Aeder
(74) Attorney, Agent, or Firm — Leason Ellis LLP

(57) ABSTRACT

The present invention relates to the sialyltransferase ST3GAL6 for use as a biomarker for multiple myeloma, and especially as a marker for myelomas with inferior survival rates. The inventors have shown that glycosylation gene expression is dysregulated in Multiple Myeloma and that overexpression of the sialyltransferase ST3GAL6 is associated with inferior survival rates in patients.

2 Claims, 20 Drawing Sheets

Specification includes a Sequence Listing.

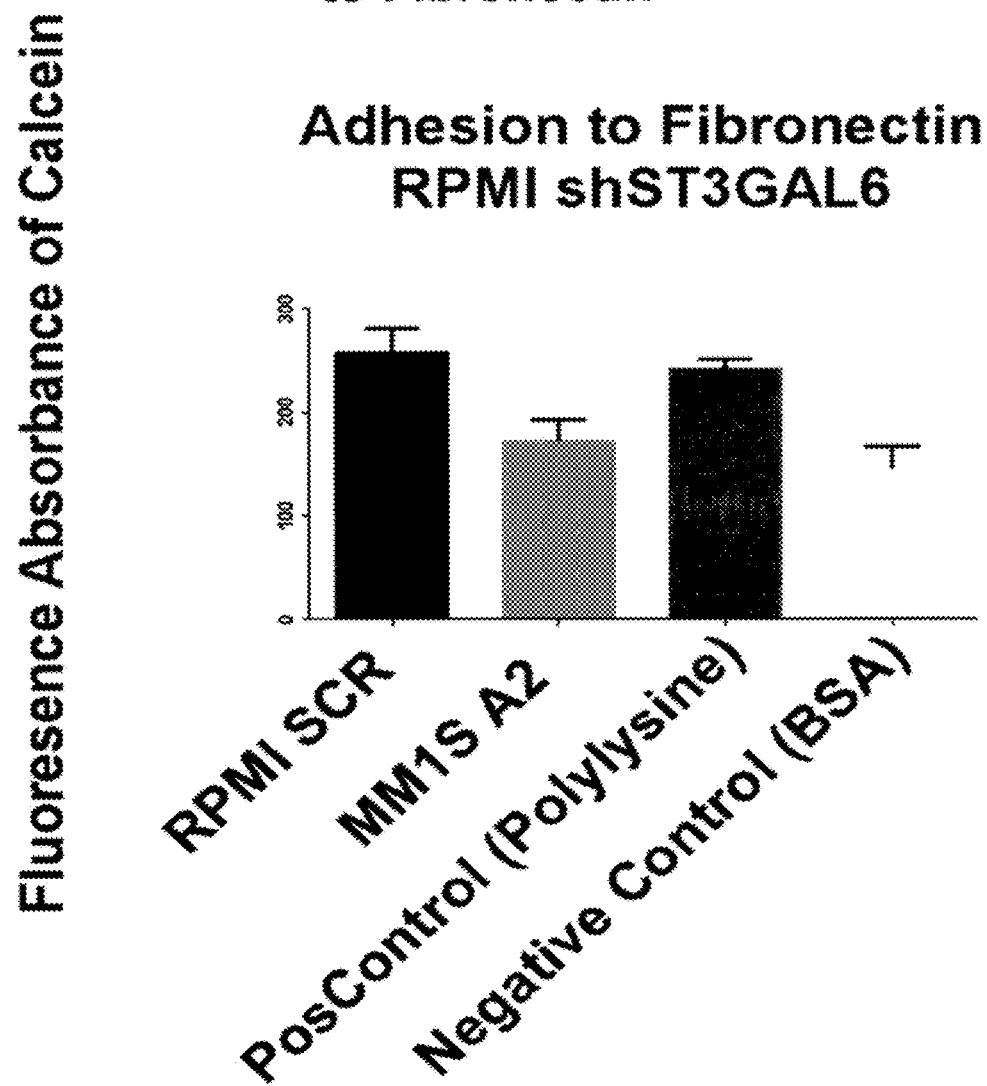

Adhesion of shST3GAL6 myeloma cell lines to primary bone marrow stromal cells taken from the bone marrow of myeloma patients

SIALYLTRANSFERASE ST3GAL6 AS A MARKER FOR MULTIPLE MYELOMA

SEQUENCE LISTING

A sequence listing, created as the ASCII text file "11201-005053US1_ST25.txt" having a file size of 2 kilobyte, is incorporated herein by reference in its entirety.

FIELD OF THE INVENTION

The present invention relates to markers for Multiple Myeloma. In particular, the invention relates to the sialyltransferase ST3GAL6 for use as a biomarker for multiple myeloma, and especially as a marker for myelomas with inferior survival rates. The inventors have shown that glycosylation gene expression is dysregulated in Multiple Myeloma and that overexpression of the sialyltransferase ST3GAL6 is associated with inferior survival rates in patients.

BACKGROUND TO THE INVENTION

Glycosylation is a stepwise procedure of covalent attachment of oligosaccharide chains to proteins or lipids. Alterations in glycosylation are associated with malignant transformation, with growing evidence implicating the dysregulation of glycosylation genes (glyco-genes) in multiple myeloma (MM). P selectin glycoprotein ligand-1 (PSGL1), recently reported to be important in MM cell adhesion and trafficking is over expressed by MM cells. Importantly, the generation of functional selectin ligands requires post-translational modification of scaffold proteins by glycosyltransferases and sialyltransferases generating selectin ligands such as Sialyl Lewis X (sLex).

ST3Gal sialyltransferases are a family of enzymes that add sialic acid to the terminus of type I, II & III glycan chains There are at least 20 different human sialyltransferases, in four major sub-groups:-ST6GalNAc I to VI, ST3Gal I to VI, ST6Gal I to II and ST8Sia I to VI. Each of these sialyltransferase genes is differentially expressed in a tissue-, cell type-, and stage-specific manner to regulate the sialylation pattern of cells. They differ in their substrate specificity, tissue distribution and various biochemical parameters: they specifically catalyze the addition of sialic acid onto different sugars with different sugar linkages (alpha 2, 3; alpha 2,6; alpha 2,8). In addition the specificity of the sialyltransferase is determined by the structure of the underlying core sugar: e.g. ST3GAL6 adds sialic acid onto the galactose part of an underlying core sugar structure, but only when galactose is joined to N-acetyl glucosamine in beta 1,4 linkage whereas ST3GAL1 will only catalyze the addition of sialic acid to galactose joined to N-acetyl galactosamine in beta 1,3 linkage etc.

ST3GAL6 can specifically sialylate type II glycan chains (Galβ1-4GlcNAc) which form critical components of sialyl Lewis X (sLe$^X$). sLe$^X$ is the carbohydrate ligand on glycoproteins and glycolipids which determines selective binding activity for selectins.

ST3GAL6 is a sialyltransferase which catalyses the transfer of sialic acid from cytidine 5-prime monophospho-N-acetylneuraminic acid (CMP-NeuAc) to terminal positions of glycoprotein and glycolipid carbohydrate groups. Terminal Neu5Ac residues are key determinants of carbohydrate structures, such as the Sialyl Lewis X. Sialyl Lewis X is a tetrasaccharide carbohydrate known to play a vital role in cell to-cell recognition. Cellular trafficking in MM is mediated in the bone marrow by selectins such as P-selectin. The common minimum binding determinant for all selectins is sialyl-Lewis X, the sialyation of this tetrasaccaride, mediated by ST3GAL6, is therefore potentially critical to myeloma biology. It has recently been shown that MM cells express high levels of P-selectin Glycoprotein Ligand-1 (PSGL-1), leading to an increased interaction of MM cells with microenvironmental cells expressing P-selectin(1). Also inhibition of P-selectin with the glycomimetic selectin inhibitor GM-1070 (Glycomimetics) can sensitize MM cells to a successful treatment for myeloma called bortezomib, which highlights the potential role of targeting glycosylation in MM.

Selectins are a family of cell adhesion molecules which have been shown to play an important role in cancer biology. There are three members of the selectin family: P-selectin expressed on activated platelets and endothelial cells, L-selectin present on leukocytes and E-selectin expressed on activated endothelial cells. Besides the accepted roles of selectins in physiological processes, such as inflammation, immune response and hemostasis, there is accumulating evidence for the potential of selectins to contribute to a number of pathophysiological processes, including cancer metastasis. Cancer cell interactions with selectins are possible due to a frequent presence of carbohydrate determinants-selectin ligands on the cell surface of tumor cells from various type of cancer. The degree of selectin ligand expression by cancer cells is well correlated with metastasis and a poor prognosis for cancer patients. There is emerging evidence that targeting selectin ligands like P-selectin glycoprotein ligand1 (PSGL1) in multiple myeloma can increase tumour cell sensitivity to current therapies.

Until recently there were no reports of the effect of ST3GAL6 deficiency on leucocyte trafficking, however, it has very recently been reported that P and E-selectin dependent leucocyte rolling was mildly reduced in ST3GAL6-null mice and more severely in double deficient mice. There have been no reports of the effect of over expression or deficiency of ST3GAL6 in in vitro or in-vivo models of multiple myeloma. Based on the above and on their work to date, the present inventors believe that ST3GAL6 may have an important role in multiple myeloma disease biology.

It has been demonstrated in cell lines from multiple myeloma patients that ST3GAL6 is upregulated in comparison to non-malignant human cell lines. It has also been demonstrated that ST3GAL6 is induced by hypoxia in myeloma cell lines MM1S, RPMI8226 and U266. Hypoxia has been shown to stimulate MM cell homing to the bone marrow microenvironment and has been associated with multiple myeloma cell dissemination. Therefore it is possible that this gene may play a role in the mechanism of these hypoxia-induced processes.

Using real time quantitative polymerase chain reaction in plasma cells (myeloma cells) selected from the bone marrow of patients with multiple myeloma, it has been shown by the present inventors that the gene is upregulated in comparison to healthy controls. A trend was observed towards higher expression of the gene in patients with more advanced multiple myeloma and in patients with relapsed disease vs those who had a stable response to therapy. Therefore ST3GAL6 could serve as a biomarker in this disease with a potential prognostic significance.

ST3GAL6 codes for a transmembrane protein localized to the Golgi apparatus which has enzymatic activity catalyzing the transfer of sialic acid to terminal positions of glycoprotein and glycolipid carbohydrate groups. The present inventors have demonstrated expression of the protein in bone marrow plasma cells from patients with multiple myeloma and demonstrated differential expression compared to normal healthy bone marrow using immunohistochemistry and a specific antibody to ST3GAL6. At the sugar level it has been demonstrated using biotinylated lectin based flow cytometry that there is an increased level of alpha 2,3 sialic acid on the surface of cultured myeloma cells. This has been confirmed using lectin based flow cytometry. Frithz et al (Eur. J. Clin. Oncol, vol 21, No. 8, pp 913-917, 1985) showed an increased serum level of sialyltransferase in multiple myeloma patients. However no identification of the actual sialyl transferase involved in the disease was undertaken in this paper. The present inventors are the first to implicate a specific sialyltransferase in pathogenesis of multiple myeloma.

The citation does not disclose the prognostic significance of any sialyltransferase or it's potential use as a biomarker of transition from MGUS to MM with increasing levels associated with disease progression.

FUCA1 is a gene that encodes the lysosomal enzyme alpha-L-fucosidase, which is involved in the degradation of fucose-containing glycoproteins and glycolipids. Mutations in this gene are associated with fucosidosis (FUCA1D), which is an autosomal recessive lysosomal storage disease.

Object of the Invention

It is an object of the present invention to provide a potential biomarker or drug target in multiple myeloma. It is also an object to use the biomarker to overcome current issues with therapy resistant disease by enabling the correct treatment to be used for a given patient or by allowing the identification of new therapeutic agents.

It is a further object to allow the development of a disease specific target in multiple myeloma. In particular it is a further object to use ST3GAL6 in the discovery of other biomarkers in multiple myeloma. It is another objective to provide prognosticly significant markers, either alone or in combination, for Multiple Myeloma. A still further object is to provide a method of identifying therapeutic agents for the treatment of multiple myeloma.

SUMMARY OF THE INVENTION

According to the present invention there is provided a method of diagnosing multiple myeloma in a patient comprising determining the levels of ST3GAL6 in a sample obtained from the patient and comparing the level determined with the level in a control sample, an increased level relative to the control indicating the presence of multiple myeloma in the patient. The control sample may be the level of ST3GAL6 in at least one healthy individual. If a healthy individual is used as a control, then a diagnosis of MM is made on the basis of an increased level of ST3GAL6 in the test sample. The skilled person will realise that the method would also work using control levels from MM patients, in which case MM can be diagnosed if the levels of ST3GAL6 in the test sample are in the same range as those of MM patients.

The invention also relates to a method of determining the prognosis of a multiple myeloma patient comprising determining the levels of ST3GAL6 in a sample obtained from the patient and comparing the level determined with the level in a control sample, an increased level compared to a healthy control is predictive of a reduced survival rate. The sample tested may be a blood, plasma or serum sample or a tissue sample. The tissue sample could be a bone marrow sample.

The invention also provides methods, kits and uses of the markers FUCA1 and ST3GAL1 in the diagnosis and assessment of prognosis of multiple myeloma as described herein for ST3GAL6. The invention also provides combinations of one or more of ST3GAL6, FUCA1 and ST3GAL1 in such methods and uses.

The level of ST3GAL6, FUCA1 and ST3GAL1 may be determined by immunohistochemistry, by RNA/DNA analysis, any form of immunoassay, including but not limited to an ELISA assay, a competitive or inhibition ELISA, a sandwich ELISA assay, a micro-array based assay, a functionalised nanoparticle assay, other rapid assay platform such as QDots, F1 tags and electro sensors, or a flow cytometry assay or a real-time chip-based assays.

In another aspect the invention provides a kit for diagnosing multiple myeloma in a patient comprising an antibody against ST3GAL6, or reagents for detecting the expression of DNA or RNA encoding ST3GAL6. Such a kit may also be used for determining prognosis of a patient with multiple myeloma comprising an antibody against ST3GAL6, or reagents for detecting the expression of DNA or RNA encoding ST3GAL6.

Also provided is ST3GAL6 for use as a marker for diagnosing multiple myeloma or for determining prognosis of a patient with multiple myeloma.

In yet another aspect the invention provides a method of screening a therapeutic agent for suitability for the treatment of multiple myeloma comprising testing a candidate therapeutic agent for the ability to reduce the expression of ST3GAL6 levels or activity of ST3GAL6 in a model system, wherein a reduction of expression or activity of ST3GAL6 indicates suitability for treatment of multiple myeloma.

Also provided is a method of reducing or alleviating multiple myeloma comprising administration of a modulator of ST3GAL6 in an amount sufficient to reduce ST3GAL6 expression or activity. The modulator may be interfering RNA specific for ST3GAL6, a selectin inhibitor or a glycosyltransferase inhibitor. The invention also provides a pharmaceutical composition comprising interfering RNA specific for ST3GAL6, a selectin inhibitor or a glycosyltransferase inhibitor together with a pharmaceutically acceptable carrier or excipient.

There appears to be deregulation of the ST3GAL6 gene as plasma cells transition from the pre-myeloma phase to active myeloma with a clear increase in ST3GAL6 mRNA in myeloma cells compared to their normal counterparts. What leads to this deregulation is the subject of ongoing investigation but one factor the inventors have found to be associated is hypoxia. Increased transcription leads to increased levels of the ST3GAL6 sialyltransferase enzyme, which can then be readily detected by immunological techniques, including immunohistochemistry, immunocytochemistry, flow cytometry, etc. The serum of patients with high intracellular levels of ST3GAL6 may also contain increased levels of the enzyme, which could be detected by ELISA. Ultimately, the high levels of this enzyme catalyze the addition of excess alpha 2,3 sialic acid residues, leading to formation of high levels of sialyl Lewis X antigen on the selectin ligands of affected cells (e.g. P-selectin ligand or CD44). The increased expression of sialyl Lewis X as a result of ST3GAL6 enzyme activity leads to increased interaction of myeloma cells with selectins (both P and E) present on endothelial cells and bone marrow stromal cells, leading to increase cell trafficking, dissemination and drug resistance. The detection of high levels of ST3GAL6 is not diagnostic of myeloma but may help identify patients with a poorer prognosis and may also identify patients with earlier stage disease (such as MGUS) who may actually be at higher risk of progression to active disease than their counterparts with normal ST3GAL6. ST3GAL6 overexpression may serve as a biomarker of response for treatment of patients with selectin inhibitors such that patients with ST3GAL6 overexpression could eventually be targeted for treatment with selectin inhibitors or other drugs interfering with the generation of selectin ligands (such as glycosyltransferase inhibitors or RNA interference approaches). ST3GAL6 overexpression has been associated with metastatic risk in colon cancer and breast cancer but not in other haematopoietic malignancies. It is quite likely it may play a role in other haematopoietic maligancies including lymphomas and acute leukaemia (both myeloid and lymphoid).

Gene Targeting

ST3GAL6 may serve as a target in multiple myeloma since reduced expression of the gene may result in inhibition of selectin mediated cellular adhesion and trafficking.

Targeting at the gene level could be mediated by a specific inhibitor of ST3GAL6 which may also have potential to induce down regulation of the gene.

Enzyme Targeting

Direct enzyme inhibition can be achieved by global inhibition of sialyltransferases using fluorinated analogs of sialic acid as has previously been demonstrated in myeloid cells, where complete loss of selectin binding and impaired leucocyte rolling was demonstrated. The sialyltransferase inhibitor AL10 inhibits adhesion, migration, actin polymerization and invasion of alpha-2,3-ST-overexpressing A549 and CL1.5 human lung cells by effectively attenuating total cell surface sialylation. This compound is a lithocholic acid analogue derived from soyasaponin I by chemical synthesis in high purity and good yield. A similar approach to sialyltransferase inhibition could be adopted and developed in multiple myeloma.

Sialic Acid Targeting

Significant reduction in rolling of sialidase treated neutrophils when exposed to E and P-selectins has been demonstrated so direct global inhibition of sialic acid on the surface of myeloma cells is likely have the same effect with a resultant reduction in adhesion.

Measurement of Sialyltransferase in Blood and Bone Marrow

Measurement of serum sialyltransferase mean activities in patients with multiple myeloma has previously been shown to be feasible. In untreated patients (as opposed to treated ones), a significantly higher serum sialyltransferase activity was shown among patients with stage III multiple myeloma in comparison to stages I and II, suggesting a link between tumour burden and enzyme activity.

Detection Methods:

ELISA;

Currently commercially available ELISA kits for the specific detection of ST3GAL6 in patient serum could be employed to detect serum levels as part of a prognostic or diagnostic test (MyBio Source catalog #MBS931514).

Flow Cytometry:

Flow cytometry analysis of CD138 microbead selected plasma cells from blood and bone marrow of multiple myeloma patients can be used to detect the presence of alpha 2,3 sialic acid on the cell surface. This can act as a surrogate marker of ST3GAL6 expression and a validation of the cell surface glycosylation status. This widely available low cost technique can be performed immediately following bone marrow aspiration and would allow efficient establishment of the alpha 2,3 sialylation status of individual patients.

The inventors have performed this technique using multiple myeloma cell line RPMI8226 and demonstrated a significant shift in median fluorescent intensity for *Maackia amurensis* agglutinin (MAA) which is specific for alpha 2,3 bound sialic acids. RPMI cells were harvested incubated with MAA lectin for 3 mins at 4 degrees (200,000 cells/well in 100 uL). Following a washing step cells were incubated with streptavadin APC and incubated×30 mins at 4 degrees. MM cells were treated with mouse anti human CD138 antibody or with an isotype control for 1 hour on ice. Expression of MAA lectin in CD138 positive cells was determined by flow cytometry analysis (BD Biosciences FACS Canto) and quantified as a ratio of the mean fluorescence intensity (MFI) of the detected target to the MFI of the isotype control.

BRIEF DESCRIPTION OF THE DRAWINGS

FIG. 5 *a* and *b*: ST3GAL6 protein can be detected by immunohistochemistry in bone marrow plasma cells from patients with multiple myeloma. FIG. 5*a* is, from a patient with multiple myeloma, while

FIG. 10A: Adhesion to fibronectin shST3GAL6. FIG. 10B: Adhesion to fibronectin RPMI shST3GAL6.

FIG. 11A: Adhesion to fibronectin shST3GAL6. FIG. 11B: RPMI shST3GAL6 adhesion to MM stroma.

FIG. 14A: Scrambled; FIG. 14B: shST3GAL6.

DETAILED DESCRIPTION OF THE DRAWINGS

Materials and Methods

Figure 1:
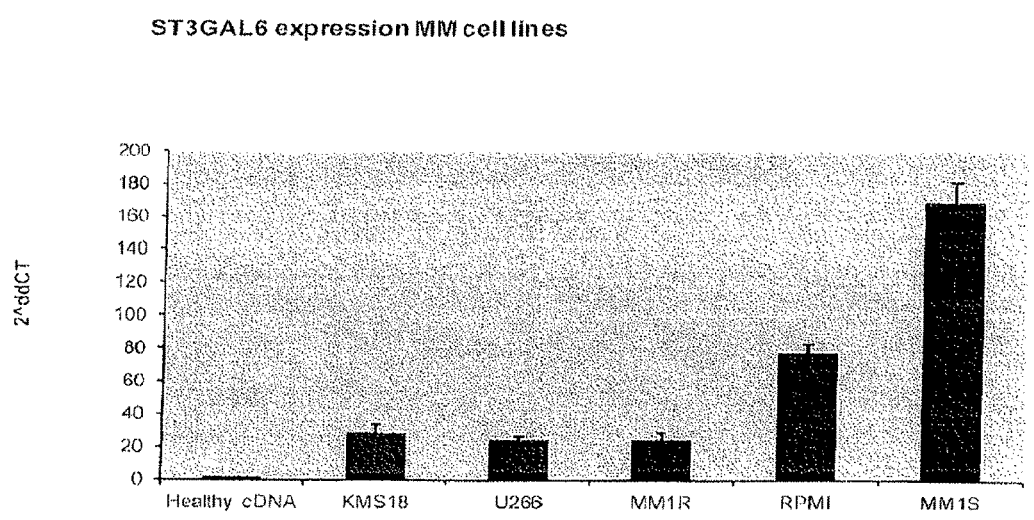
FIG. 1: The ST3GAL6 gene is overexpressed in multiple myeloma cell lines.

Real time quantitative PCR (RT_PCR) in the MM cell lines RPMI8226 and MM1R and in primary MM patient CD138 positive cells was used to examine expression of the ST3GAL6 gene. The prognostic significance of the ST3GAL6 gene was analyzed using Kaplan Meier survival estimates. Membrane protein extracts from MM cell lines were applied directly to lectin microarrays following fluorescent labelling to generate cell surface glycan profiles. Protein expression was assessed by immunohistochemistry (IHC) on primary MM bone marrow sections from MM patients and healthy controls. Lectin based flow cytometry was carried out to assess for the binding of sialic acid lectins to MM cell line RPMI8226.

CD138 Cell Isolation

Bone marrow aspirates were obtained from multiple myeloma patients at Galway University Hospital following informed consent. The mononuclear fraction of the bone marrow aspirate was isolated using Ficoll Paque™ Plus (STEMCELL Technologies) and high speed zero brake centrifugation. PC isolation from mononuclear cell fraction was performed by immunomagnetic bead selection with monoclonal mouse antihuman CD138 antibodies using the AutoMACs automated separation system (Miltenyi-Biotec. Auburn, Calif.). PC purity of more than 95% homogeneity was confirmed by 2-color flow cytometry using CD1381/CD452 and CD381/CD452 criteria (Becton Dickinson, San Jose, Calif.).

Real Time Quantitative Polymerase Chain Reaction (RT_PCR)

The mRNA expression of ST3GAL6 was detected by RT-PCR in indicated MM cell lines and in sorted CD138+ cells from MM patients with the forward primer TTG CCT CTC TGC TGA GGT TT and the reverse primer CCT CCA TTA CCA ACC ACC AC The expression of GAPDH or 18S was detected with their respective primers. RT-PCR amplification was carried out with 100 ng of cDNA in a 10-μl reaction mixture containing 5 ul SYBR green mix (Bio-Rad, Mississauga, ON) and 0.2 ul qPCR primers (SA Bioscences, Frederick, Md.). Data quantification was carried out by the deltadeltaCT method.

Lectin Array

Glycan-binding proteins (Lectins) conjugated to microarrays were used to probe compositions and differential presence of glycan residues on glycoconjugates and cells. The glycan samples were fluorescently tagged prior to hybridization step to co-incubate glycan samples and lectins. After hybridization, slides were washed extensively and scanned in a microarray scanner. The lectin-glycan binding data is analyzed using commercially available software.

Sialyltransferase Serum Assay

This assay employs the quantitative sandwich enzyme immunoassay technique. Antibody specific for ST3GAL6 has been pre-coated onto a microplate. Standards and samples are pipetted into the wells and any ST3GAL6 present is bound by the immobilized antibody. After removing any unbound substances, a biotin-conjugated antibody specific for ST3GAL6 is added to the wells. After washing, avidin conjugated Horseradish Peroxidase (HRP) is added to the wells. Following a wash to remove any unbound avidin-enzyme reagent, a substrate solution is added to the wells and color develops in proportion to the amount of ST3GAL6 bound in the initial step. The color development is stopped and the intensity of the color is measured.

Immunohistochemistry

To detect ST3GAL6, BM aspirates from 55 MM patients and 3 healthy subjects were rinsed with PBS, fixed with 4% formaldehyde in PBS, dehydrated with ethanol, embedded in paraffin, and sectioned. Tissues were then immunostained with mouse anti-human ST3GAL.

Knockdown of ST3GAL6 in Myeloma Cell Lines;

Green Fluorescent Protein (GFP) Luc$^+$-MM1s cells have been generated using lentiviral infection and cultured at 37° C. in RPMI 1640 medium containing 10% FBS (Sigma-Aldrich), 2 mM L-glutamine, 100 U/mL of penicillin, 100 μg/mL of streptomycin (Invitrogen) and 100 μg/mL Geneticin. Plasmids were routinely amplified in the *Escherichia coli* DH5_strain and isolated from cultures by using the Qiagen Plasmid Spin Midiprep Kit (Qiagen, Valencia, Calif.).

Scrambled shRNA control plasmids can be generated using the same methods used to generate lentivirus. Scrambled lentivirus is used to infect MM1s cell to act as a control in these experiments. Stable knockdown of ST3GAL6 can be achieved in these cells using a plasmid generated lentiviral vector which infects the MM is cells.

Interfering RNA Screening

IRNA screening is performed in cultured MM cell lines as a lethality study. Using technology available from the Broad Institute Boston Mass., USA siRNAs targeting individual human silayltransferase genes are preprinted on 384-well plates alongside staggered negative and positive control siRNA. Primary screening experiments are conducted in duplicate on separate occasions for several cultured MM cell lines. For each experiment, plates preloaded with siRNA and frozen were thawed at room temperature and 20_L/well-diluted Lipofectamine 2000 or Dharmafect 3 solution is added to the relevant wells. After 30 minutes, MM cells are added to each well. Cell viability is determined at 96 hours by CellTiter-Glo luminescence assay read on a BMG Polar-star machine using excitation 544-nm/emission 590-nm filters. Surviving knock down cells can be analysed by the following methods.

Cellular Adhesion Assays;

BMSCs are cultured overnight to confluence in 96-well plates (5_103 cells/well) before initiating the adhesion assay. MM1s cells are serum-starved for 3 hours, prelabeled with GFP, added to the BMSCs (1_105 cells/well), and allowed to adhere for 2 hours at 37° C. Nonadherent cells can be aspirated away, the BMSCs washed, and fluorescence intensity measured using a fluorescent-plate reader (Ex/Em_485/520 nm).

Transendothelial Migration and Chemotaxis of MM Cells

HUVECs (5_103 cells/basket) are incubated overnight in the upper chamber of 8-micron pore filters (Costar; Corning) before performing the adhesion assay. MM1s cells are serum-starved for 3 hours and then added to the upper chamber of the basket (2_105 cells/well), and left to migrate for 4 hours at 37° C. toward the lower chamber, which contains 0 or 30 nM of SDF1_. This analysis is performed separately for ST3GAL6 knockdown cells vs scrambled control.

Assessment of Multiple Myeloma Tumour Burden in SCID Mice;

This is carried out according to methods developed by David Scadden's group (13). In vivo confocal microscopy is used to test the homing of MM1s cells to the BM in vivo and to assess the tumour burden of GFP-labelled MM1s cells (1_106) injected into anesthetized SCID mice. In some experiments mice may be pretreated with vehicle or a drug of interest 1 hour before the cell injection. A skin flap is made in the scalps of the mice to expose the underlying skull surface and Evan's blue dye is injected intravenously immediately before imaging to visualize blood vessels. High-resolution images with cellular detail are captured 30 minutes after cell injection through the intact mouse skull at depths of up to 250_m from the surface of the skull using a 30_0.9-numerical aperture water-immersion objective lens (Lomo). Multiple imaging depths were acquired and a maximum intensity z-projection is performed in ImageJ software to merge the images. GFP labelled MM cells and Evan's blue dye are excited with 491-nm and 638-am single-photon lasers and detected via 528/19-nm and 680/25-nm bandpass filters, respectively.

Materials and Methods ST3GAL6 Study:

In-Vitro Studies:

Cell Lines & Reagents:

The RPMI-8226 cell lines were purchased from ATCC (Manassas Va.) cultured in RPMI 1640 (Sigma Chemical, St. Louis, Mo.) containing 10% foetal bovine serum, 2 mmol/L L-glutamine (Life Technologies, Grand Island, N.Y.), 100 units/mL penicillin, and 100 Ag/mL streptomycin (Life Technologies). GFP-Luciferin-Neo MM1s cells were generated using a lentiviral infection method as described [1]. Primary MM cells were obtained from bone marrow samples from patients using CD138+ microbead selection (Miltenyi Biotech, Auburn Calif.) as previously described [2]. Bone marrow stromal cells (BMSC's) were obtained from healthy donor and MM patient fresh bone marrow samples and isolated as described [3]. BMSC's were then cultured in DMEM (Sigma Chemical, St Louis, Mo.) supplemented with 10% heat-inactivated foetal bovine serum, 100 units/Ml penicillin, 10 Ag/mL streptomycin (Life Technologies; 0.01%), and 2 mmol/L L-glutamine (1%; Life Technologies). Informed consent was obtained from all patients in accordance with the Declaration of Helsinki. Approval of these studies was obtained by the Dana-Farber Cancer Institute Institutional Review Board. Bortezomib was obtained from Millennium Pharmaceutical (Cambridge, Mass.), and SDF-1 was obtained from R&D Systems (Minneapolis, Minn.).

shRNA Meditated ST3GAL6 Gene Silencing:

To determine the role of ST3GAL6 in MM biology we established ST3GAL6 knockout RPMI-8226 and MM1s-GFP-Luc cell lines using a lentiviral system as previously described [4]. A plasmid based system was used to achieve knockdown of ST3GAL6 in the MM cell lines. Lentiviral ST3GAL6 shRNA and non target scrambled control shRNA was produced in HEK293T packaging cells, concentrated at different MOIs and then individually added into MM-cell suspensions in the presence of 8 mg/mL polybrene and transduced for 24 hours followed by selection in puromycin (2 mg/mL; Invitrogen). The efficiency of ST3GAL6 knockdown was assessed by flow cytometry and RT-PCR using the following primers Forward Primer; TTG CCT CTC TGC TGA GGT TT Reverse Primer, CCT CCA TTA CCA ACC ACC AC [5]. The resultant stable ST3GAL6 knockdown (shST3GAL6) cell line is compared to the scrambled control cell line in all subsequent functional assays. The sense and antisense oligonucleotide sequence for construction of ST3GAL6 shRNA were as follows: clone no 10402; [NM_006100.2-1332s1c1, target sequence CCTTTGCAC-TACTATGGGAAT (A2), NM_006100.2-1110s1c1 target sequence CCAGCCTTAAACCTGATTTAT (A3)]

Adhesion Assays:

Assays for adhesion of MM cells to normal and MM BMSC's were performed using 96-well plates ($5\times10^3$/well). Normal or MM BMSC's (5,000)/well) were seeded in 96-well plates overnight in supplemented DMEM media to establish a confluent monolayer. MM cells were serum starved overnight, prelabelled with calcein AM and added to the BMSC's and allowed to adhere for 2 hours at 37° C. Nonadherent cells were aspirated off, BMSCs were washed with PBS, and fluorescence intensity was measured using a fluorescent-plate reader (Ex/Em_485/520 nm). Fibronectin adhesion assays were performed using an in vitro adhesion assay coated with fibronectin following the manufacturer recommendations (EMD Biosciences, San Diego, Calif.) as previously described 161. Bovine serum albumin (BSA)-coated wells served as negative controls. In some of the above experiments MM cells were pre-incubated with increasing concentrations of bortezomib (0, 2.5, and 5 nM) prior to assessment of adhesion.

Migration Assays:

Migration assays were performed as previously described [6] [7]. Migration ability of MM scrambled control cells vs. shST3GAL6 cells was assessed using a transwell migration assay plate (pore size 0.8_m; Corning Life Sciences, Acton, Mass.) according to the manufacturer's instructions. MM cells were serum starved for 4 hours and following calcein AM labelling were then placed in the upper migration chambers. SDF-1_(30 nM) was added to 500_uL of RPMI 1640 in the lower chambers. After 4 hours at 37° C. cells that migrated to the lower chambers were counted on a fluorescent plate reader (Molecular Devices).

Immunoblotting:

Immunoblotting was performed as previously described [8]. Briefly, whole-cell lysates were subjected to sodium dodecyl sulfate-polyacrylamide gel electrophoresis (SDS-PAGE) and transferred to polyvinyldene fluoride (PVDF) membrane (Bio-Rad Laboratories, Hercules, Calif.). The antibodies used for immunoblotting included anti-ST3GAL6 produced in rabbit (Sigma-Aldrich, MO, USA) and anti-Actin (Cell Signaling Technology)

Immunohistochemistry:

To detect ST3GAL6, BM aspirates from 50 MM patients and 10 healthy subjects were rinsed with PBS, fixed with 4% formaldehyde in PBS, dehydrated with ethanol, embedded in paraffin, and sectioned. Tissues were then immunostained with mouse anti-human ST3GAL6 antibody and mouse-antihuman-CD138.

In-Vivo Xenograft Models

Animals:

Approval of these studies was obtained by the Dana-Farber Cancer Institute and Massachusetts General Hospital Institutional Animal Care and Use Committees. Female, 6 to 7 weeks old, severe combined immunodeficient beige (SCID-Bg) mice were obtained from Taconic Laboratories. Anesthesia was performed by intraperitoneal injections of ketamine (Bedford Laboratories, Bedford, Ohio)/xylazine (Lloyd Laboratories, Shenandoah, Iowa) at 80 mg/kg/12 mg/kg body weight prior to in-vivo imaging sessions. Following this mice were killed by inhalation of $CO2$.

Xenograft Models:

Tumors were established in mice using MM1s-GFP-Luc cells ($5\_10^6$/mouse) which were injected into the tail vein of 12 SCID-Bg mice (n=6/group).

BLI:

To detect tumor burden on a weekly basis following injection mice were injected with 75 mg/kg luciferin (Xenogen, Hopkinton, Mass.) and imaged for bioluminescence 5 minutes after the injection. The home-built bioluminescence system used an electron multiplying CCD (Andor Technology, Belfast, United Kingdom) with an exposure time of 15 seconds, an electron multiplication gain of 500-voltage gain_200, 5-by-5 binning, and background subtraction. Images were analyzed with the use of ImageJ software (National Institutes of Health, Bethesda, Md.).

In-vivo confocal: Using the above SCID-Bg xenograft mice homing of MM cells to distant bone marrow niches was tracked in vivo, by using in vivo confocal microscopy [9]. Briefly, MM cells homing to the BM were imaged in vivo using a Zeiss 710 confocal system (Carl Zeiss Microimaging, Jena, Germany) on an upright examiner stand with a custom stage. A skin flap was made in the scalp of the mice to expose the underlying dorsal skull surface. High-resolution images with cellular detail were be obtained through the intact mouse skull at depths of up to 250 μm from the surface of the skull using a 10×0.45NA Plan-Apo objective (Carl Zeiss Microimaging). Multiple imaging depths were acquired, and a maximum intensity z-projection was performed in Image J to merge the images. GFP was excited with the 488 nm line on an Argon laser. Blood vessels were imaged using Evans Blue (Sigma-Aldrich, St. Louis. Mo.) excited with a 633 nm laser. Emission signals were be collected by the Zeiss internal confocal Quasar detectors.

Results

The sialyltransferase ST3GAL6 (ST3 beta-galactosidase, alpha-2,3-sialyltransferase 6), which plays a critical role in generation of functional selectin ligands such as sLex, was upregulated in MM (fold change=2.67) and smoldering MM (fold change=2.22) but was absent in MGUS (Monoclonal gammopathy of undetermined significance). Patients from GSE24080 (n=S09) were stratified into two groups based on their expression intensities for ST3GAL6. Patients with higher normalized intensity values corresponding to probeset ID 210942_s_at (ST3GAL6) were found to have a lower median survival compared to their lower expressing counterparts. The difference in survival observed was 5.13 months (p<0.001 CI 1.3, 8.9). The association with reduced survival was independently verified in the MRC Myeloma IX microarray dataset (n=260). In this dataset using the median expression of ST3GAL6 as a cutoff there was a statistically significant reduction on overall survival with higher expression of ST3GAL6 (median OS 35.7 vs 48 months, log rank test p=0.04).

RT-PCR analysis validated the over expression of ST3GAL6 in MM cell lines and primary samples compared to healthy controls. We observed a trend for higher fold changes for ST3GAL6 in samples from patients with relapsed/refractory disease compared to those with responsive disease. IHC for ST3GAL6 on primary bone marrow sections from MM patients (n=27), demonstrated specific Golgi staining compared to controls. Consistent with the over expression of ST3GAL6 lectin microarray analysis of membrane protein extracts from MM cell lines RPMI8226 and MM1R showed binding to sialic acid-specific lectins *Maackia amurensis* agglutinin (MAA), which is specific for α2-3 bound sialic acids, and *Sambucus nigra* (SNA) which is specific for α2-6 bound sialic acids. This pattern was confirmed using biotinylated lectin based flow cytometry, which demonstrated a shift in allophycocyanin (APC) median fluorescence intensity for these lectins on RPMI8226 cells.

Figure 2:
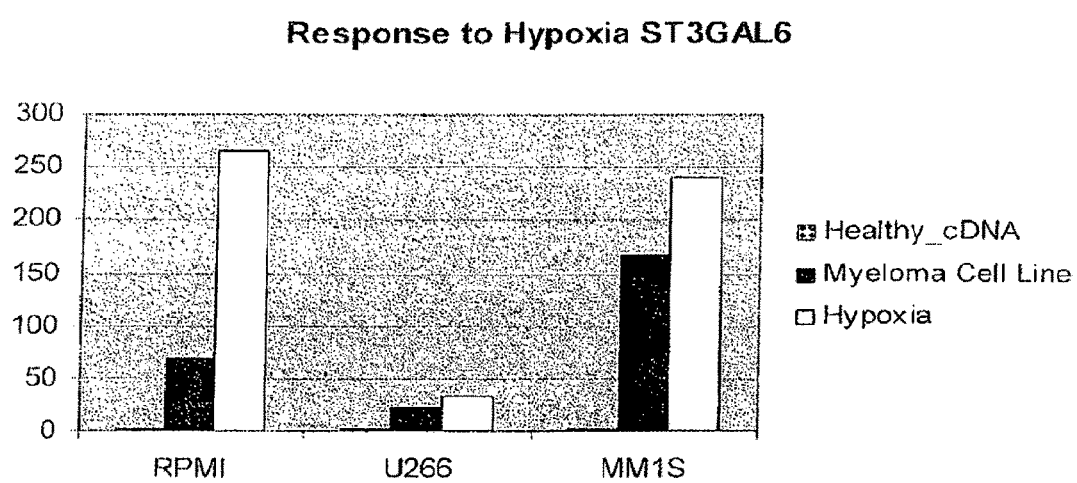
FIG. 2: ST3GAL6 gene expression is upregulated in response to hypoxia.
Figure 3:
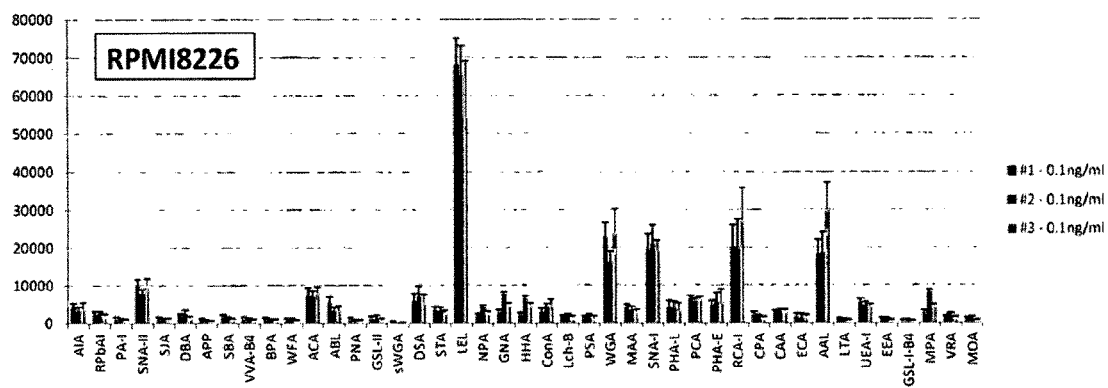
FIG. 3: Membrane proteins from multiple myeloma RPMI8226 cells are heavily sialylated consistent with increased activity of the sialyltransferase ST3GAL6.
Figure 4:
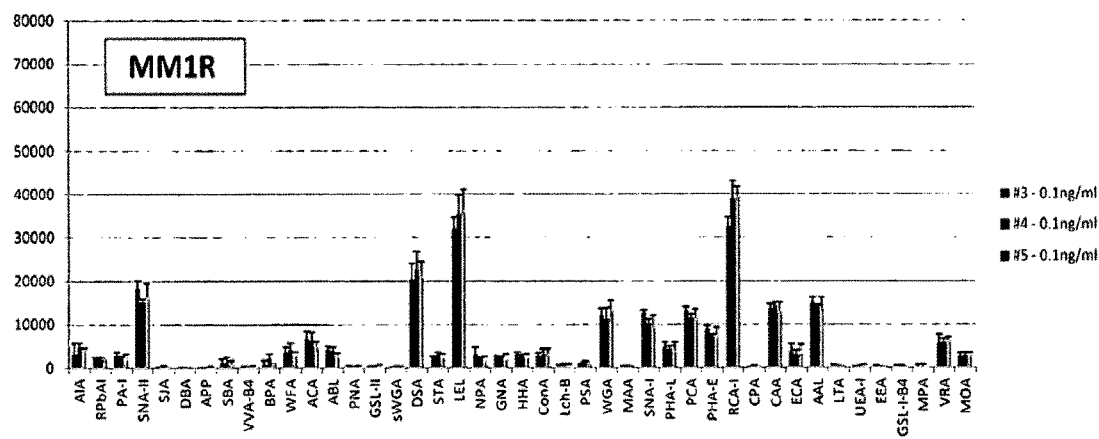
FIG. 4: Membrane proteins from multiple myeloma MM1R cells are heavily sialylated consistent with increased activity of the sialyltransferase ST3GAL6.

As shown in FIG. 1 quantitative PCR was used to detect mRNA for ST3GAL6 in CD138 plasma cells from normal donors as well as 5 different multiple myeloma cell lines. FIG. 2 demonstrates the effect of hypoxia (cells grown in hypoxic chamber with 1% $O_2$) on the gene expression of ST3GAL6 as assessed by quantitative PCR on 3 different multiple myeloma cell lines. FIGS. 3 and 4 demonstrate the pattern of lectin binding to membrane proteins from the multiple myeloma cell lines RPMI8226 and MM1R using a lectin array. This pattern of lectin binding indicates that the membrane proteins are heavily sialylated.

Figure 5A:
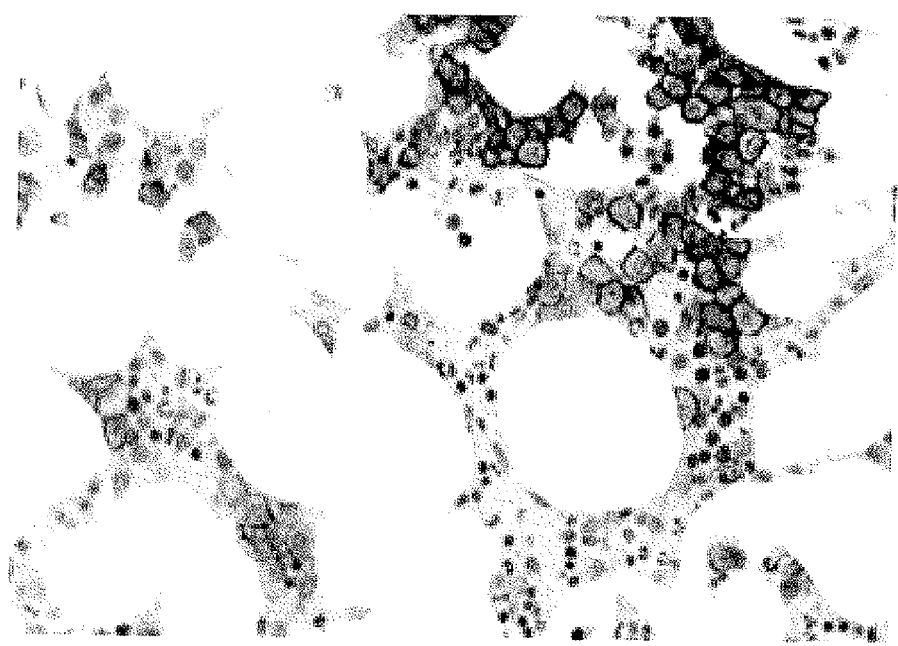
Figure 5B:
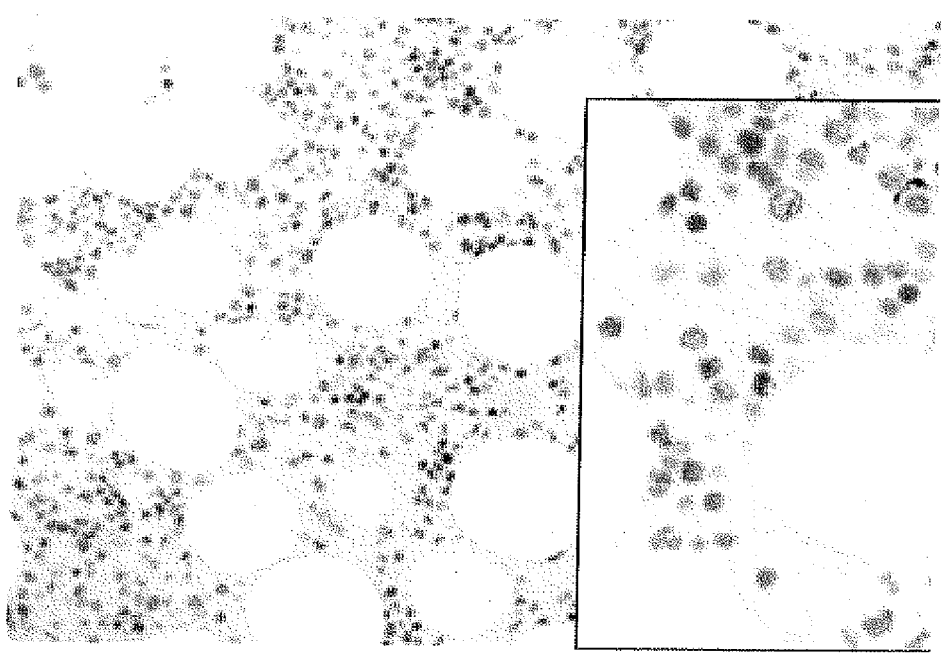
FIG. 5*b* is from a normal bone marrow
Figure 6:
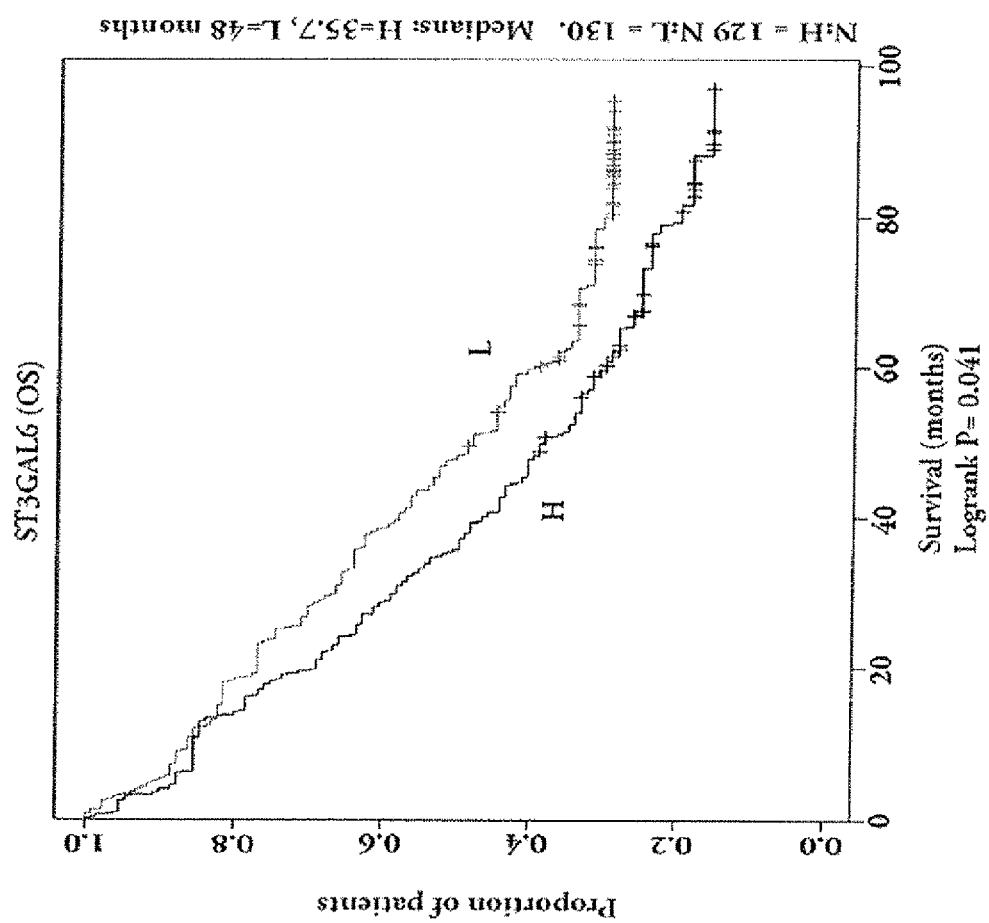
FIG. 6: Increased gene expression of ST3GAL6 is associated with inferior overall survival in the UK MRCIX Myeloma clinical trial.

FIG. 5 *a* and *b* show co-expression of CD138 and ST3GAL6 by immunohistochemistry. FIG. 5*a*, from a patient with multiple myeloma shows an excess of bone marrow plasma cells with expression of ST3GAL6 in CD138 positive cells. On the other hand, FIG. 5*b*, from a normal bone marrow, shows absence of ST3GAL6 in CD138 cells, which are present at low frequency in the marrow. Increased gene expression of ST3GAL6 is associated with inferior overall survival in the UK MRCIX Myeloma clinical trial, as shown in FIG. 6 which shows two separate Kaplan Meier survival curves for the 259 patients treated on the UK MRCIX Myeloma clinical trial according to whether they had high or low levels of expression of ST3GAL6. The 129 H patients had expression values above the median while the 130 L patients had expression values below the median. The difference in survival between the 2 groups was compared using the logrank test and is statistically significant. In patients with the highest levels of gene expression of ST3GAL1 (top 25%) there is significantly worse progression free survival. The highest levels of ST3GAL1 gene expression are seen in patients with recognised poor risk chromosome abnormalities, including t(4;14) translocation and hypodiploidy, identification of which are a standard part of the work up of myeloma patients.

Figure 7:
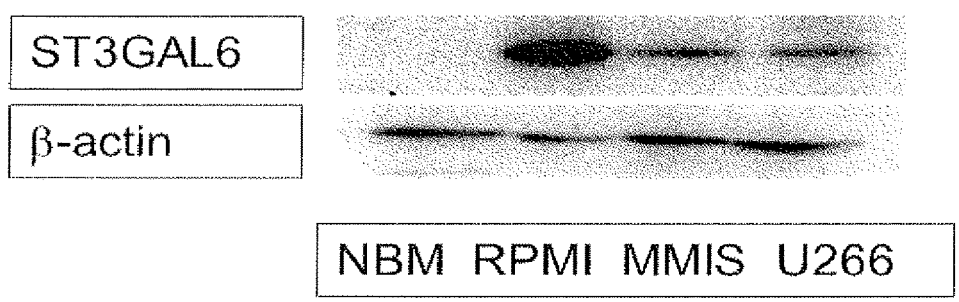
FIG. 7: ST3GAL6 protein is strongly expressed by multiple myeloma cell lines.

FIG. 7 shows protein expression of ST3GAL6 by Western blotting in normal CD138 bone marrow derived plasma cells compared with ST3GAL6 protein expression in 3 multiple myeloma cell lines. While no appreciable band can be seen in the normal plasma cells, a strong band is seen in all 3 cell lines.

Figure 8A:
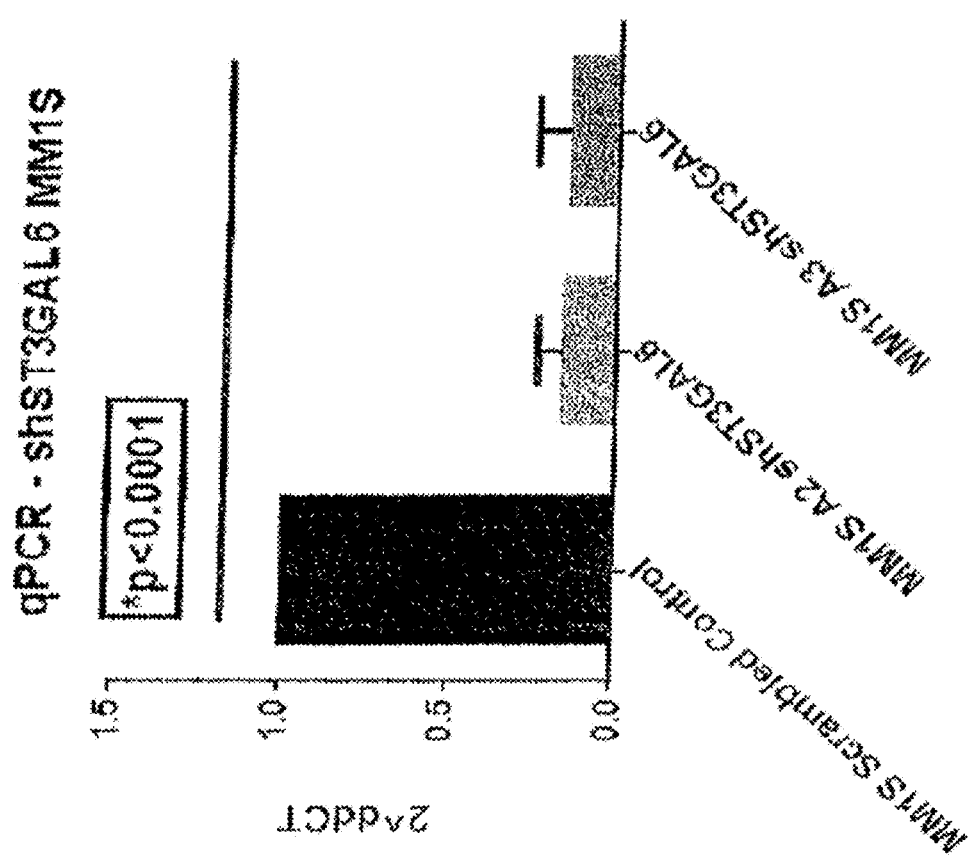
FIG. 8A: QPCR data for MM1s cells infected with a silencing lentivirus construct to ST3GAL6 in comparison to the ST3GAL6 mRNA level in a scrambled control, (FIG. 8B) the reduction of the mRNA level in the RPMI-8226 cell line. A1, A2, A3 and A4 represent different lentivaral constructs.
Figure 8B:
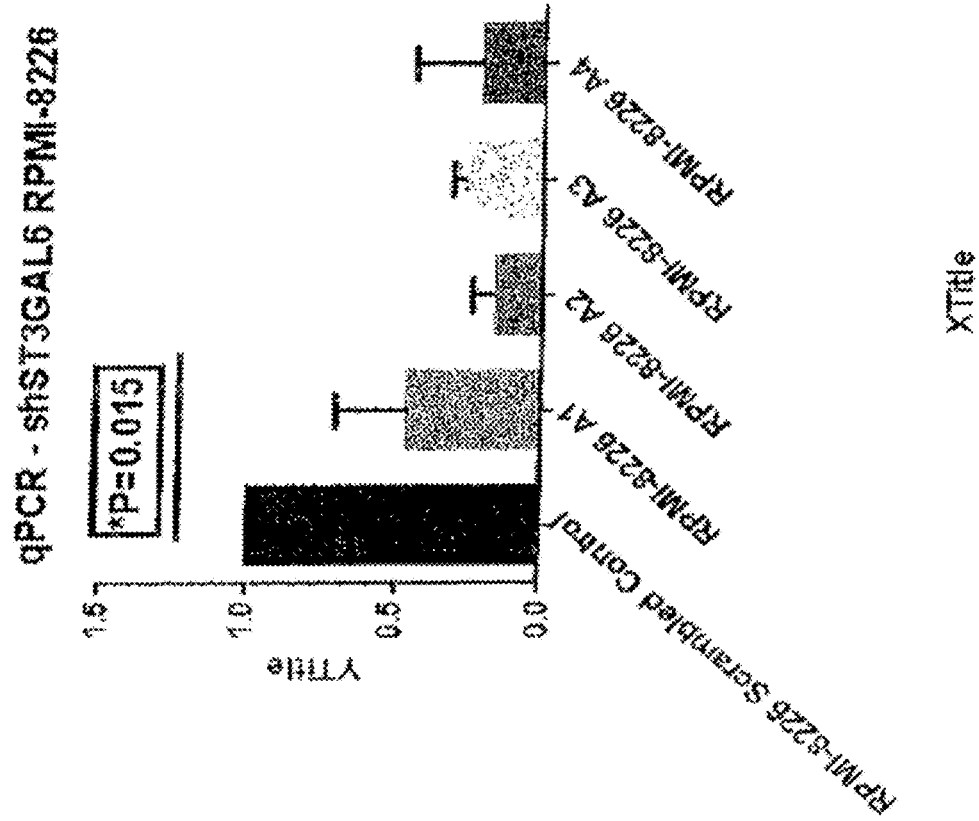

To directly identify the biological role of ST3GAL6 in myeloma, lentivaral stocks were produced from hairpin-pLKO.1 plasmids and transfected into myeloma cell lines MM1s-green fluorescent protein-luciferase positive (GFP-Luc) and RPMI-8226. The MM1s-GFP-Luc cell line was chosen in order to create a stable shST3GAL6 cell line that was amenable to later in-vivo imaging and Confocal imaging. The RPMI-8226 cell line was chosen as a representative cell line of multiple myeloma which had not been previously manipulated. As FIG. 8A shows, QPCR data for the MM1s cell line demonstrates the reduced level of mRNA detectable in cells that had been infected with a silencing lentiviral construct to ST3GAL6 in comparison to the ST3GAL6 mRNA level in a scrambled control. FIG. 8B demonstrates the effective reduction of the mRNA level in the RPMI-8226 cell line.

Figure 9:
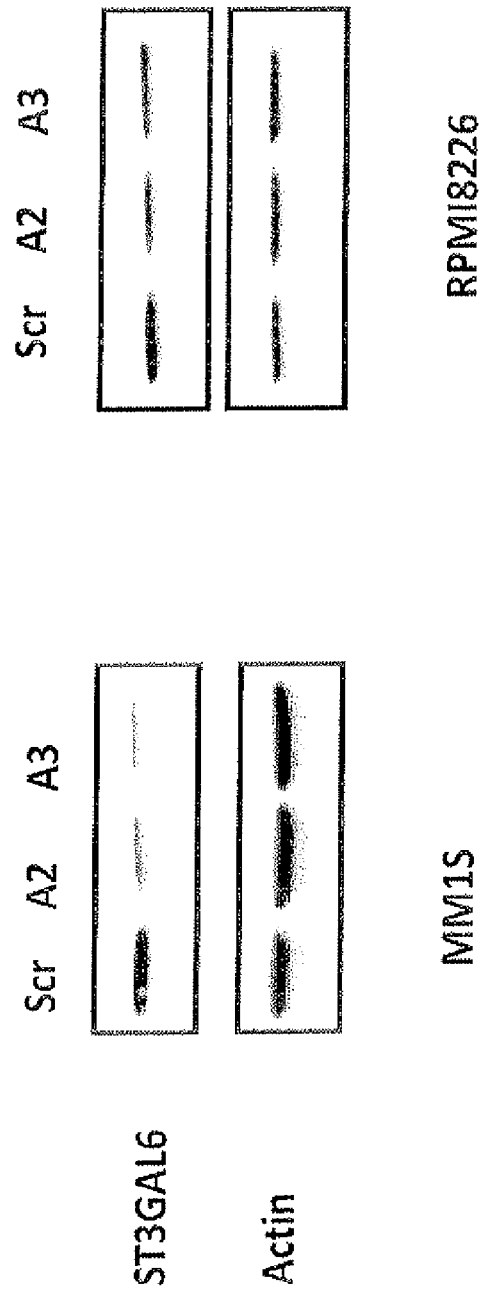
FIG. 9 Western blots of shST3GAL6 multiple myeloma cell lines.
Figure 10:
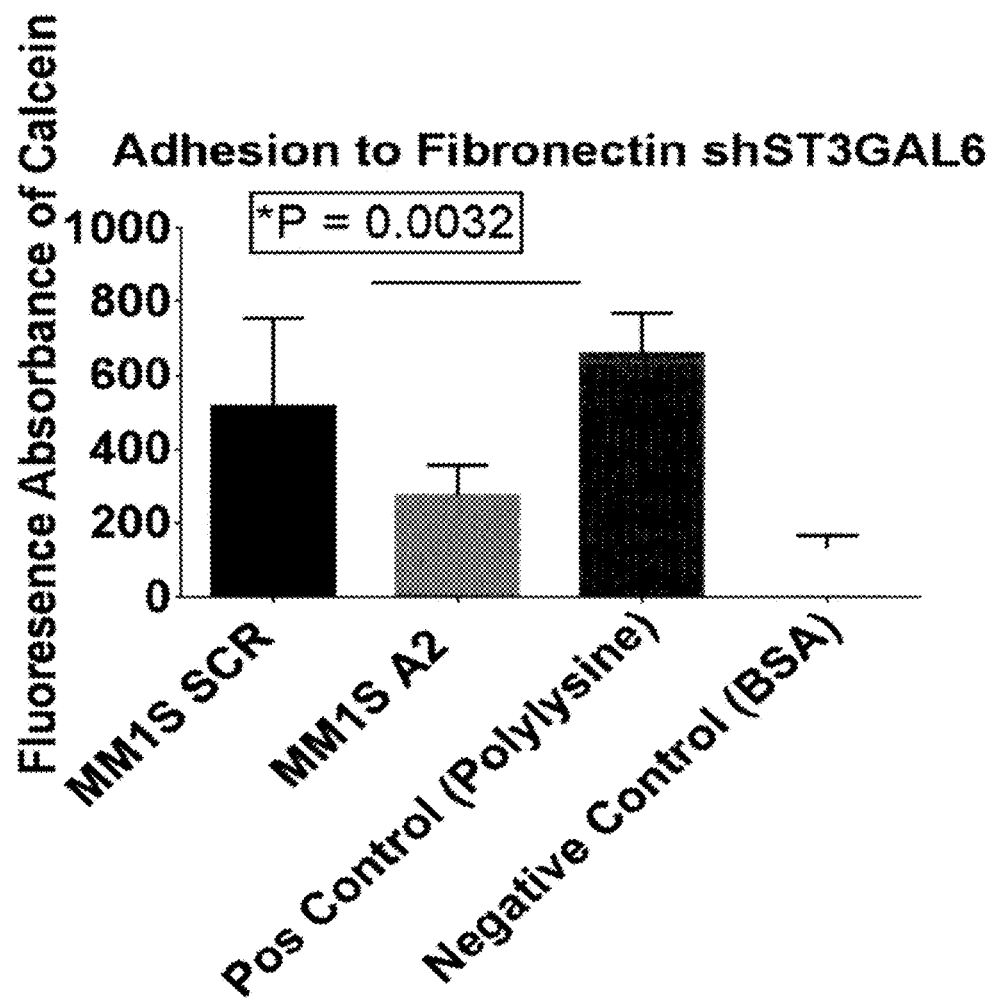
FIGS. 10A and 10B. Adhesion of shST3GAL6 myeloma cell lines to fibronectin.

Western blots demonstrating the reduced level of protein detected in the shST3GAL6 stable cell lines in comparison to respective scrambled controls are shown in FIG. 9. In-vitro functional studies were undertaken to determine the role of ST3GAL6 on MM-cell adhesion, migration and survival. The results of the adhesion analysis to fibronectin are shown in FIGS. 10A and 10B. MM cells were serum starved overnight (5×10$^5$/ml) and then incubated with calcein-acetoxymethyl ester (AM) for 30 mins at 37° C., washed and re-suspended in serum free clear RPMI media. 100 ul of cells were added to fibronectin coated 96-well plates (Calbiochem ECM Cell Adhesion Assay) for 1 hour at 37° C. After a gentle wash in PBS the fluorescence was read using a fluorescent plate reader (ex/em 485/520 nm).

Figure 11:
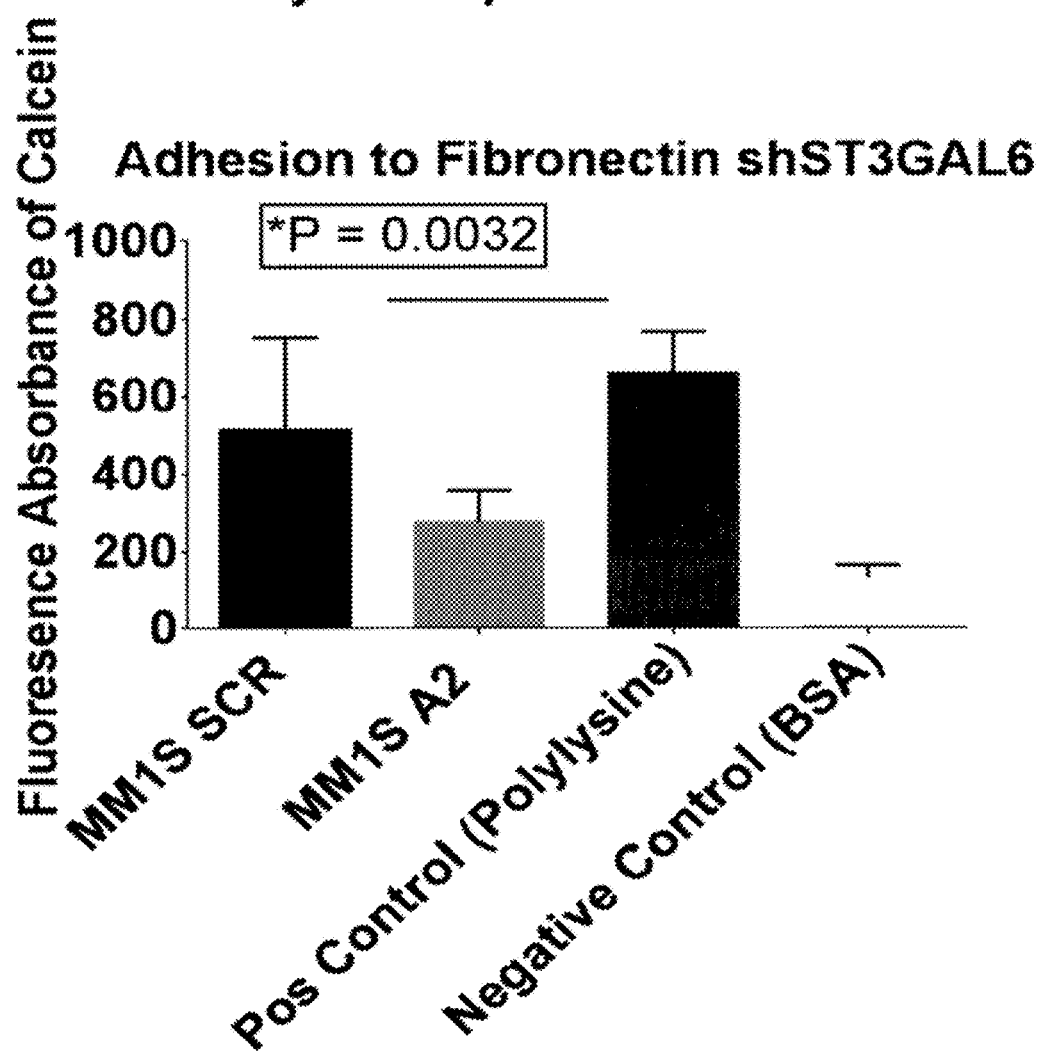
FIGS. 11A and 11B. Adhesion of shST3GAL6 myeloma cell lines to primary bone marrow stromal cells taken from the bone marrow of myeloma patients.
Figure 11:
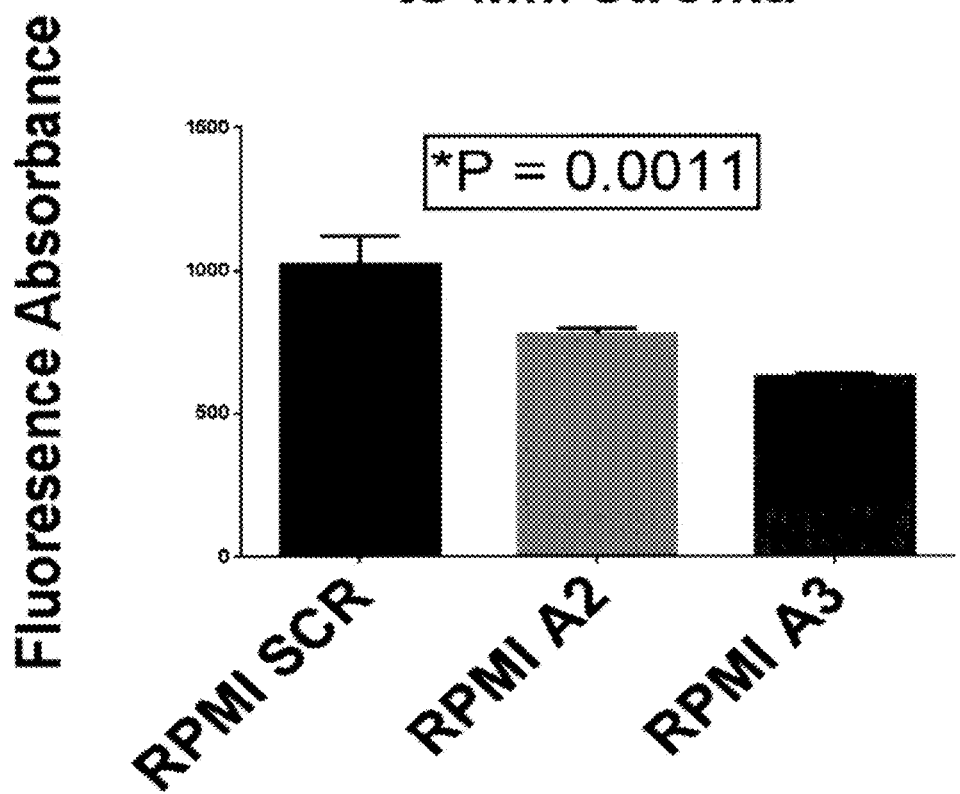
Figure 12:
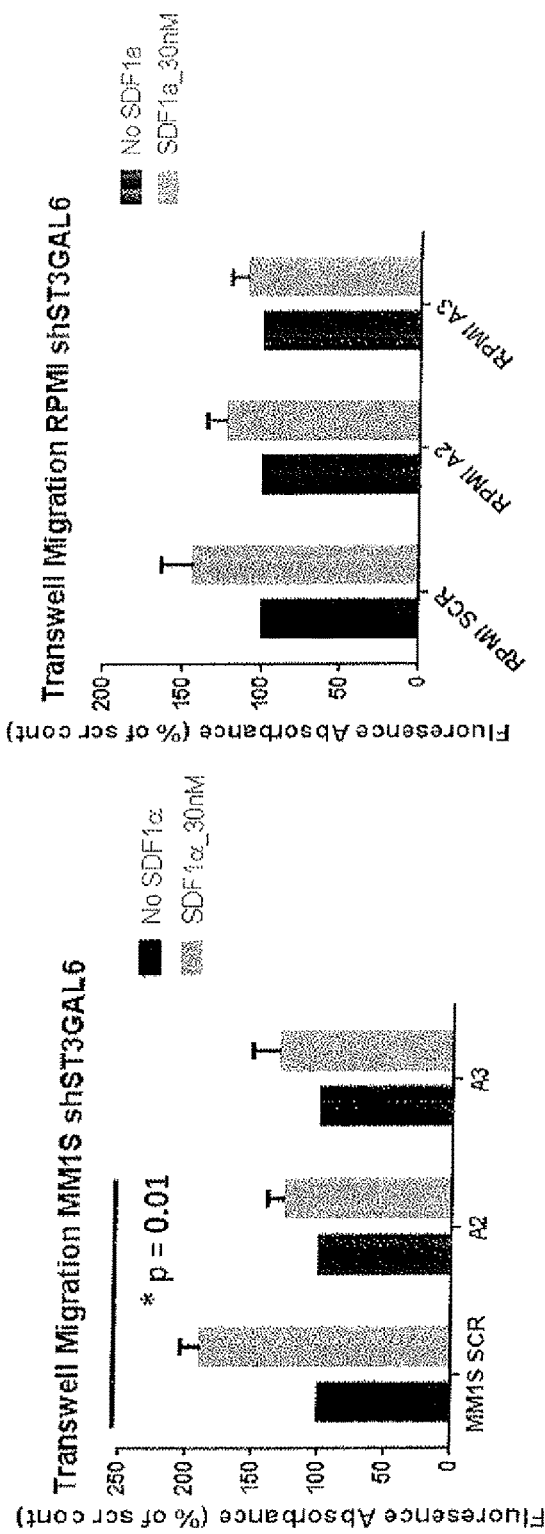
FIG. 12. Transwell assay assessing the ability of shST3GAL6 cells to migrate to the chemokine SDF-1α migration.

The results of the adhesion analysis to primary bone marrow stromal cells are shown in FIGS. 11A and 11B. MM cells were serum starved overnight and (5×10$^{5/ml}$) following this were incubated with calcein-AM as described for 30 mins at 37° C., washed and re-suspended in serum free clear RPMI media. 100 ul of cells were added to BMSC coated 96-well plates (3×10$^4$/well) for 2 hours at 37° C. After a gentle wash with PBS the fluorescence was read using a fluorescent plate reader (ex/em 485520 nm). Results of the migration studies are shown in FIG. 12. For migration studies cells (5×10$^5$) were serum starved×4 hours in clear serum free RPMI media, labelled with calcein-AM as described and added to the upper wells of transwell plates (Costar Corning pore size 0.8 μm) with serial concentrations of SDF-1α (0-30 nM) added to the 500 ul of RPMI 1640 serum free media in the lower chambers. After 4 hours at 37° C. the upper chambers were removed and cells that had migrated to the lower chambers were counted on a fluorescent plate reader.

Figure 13:
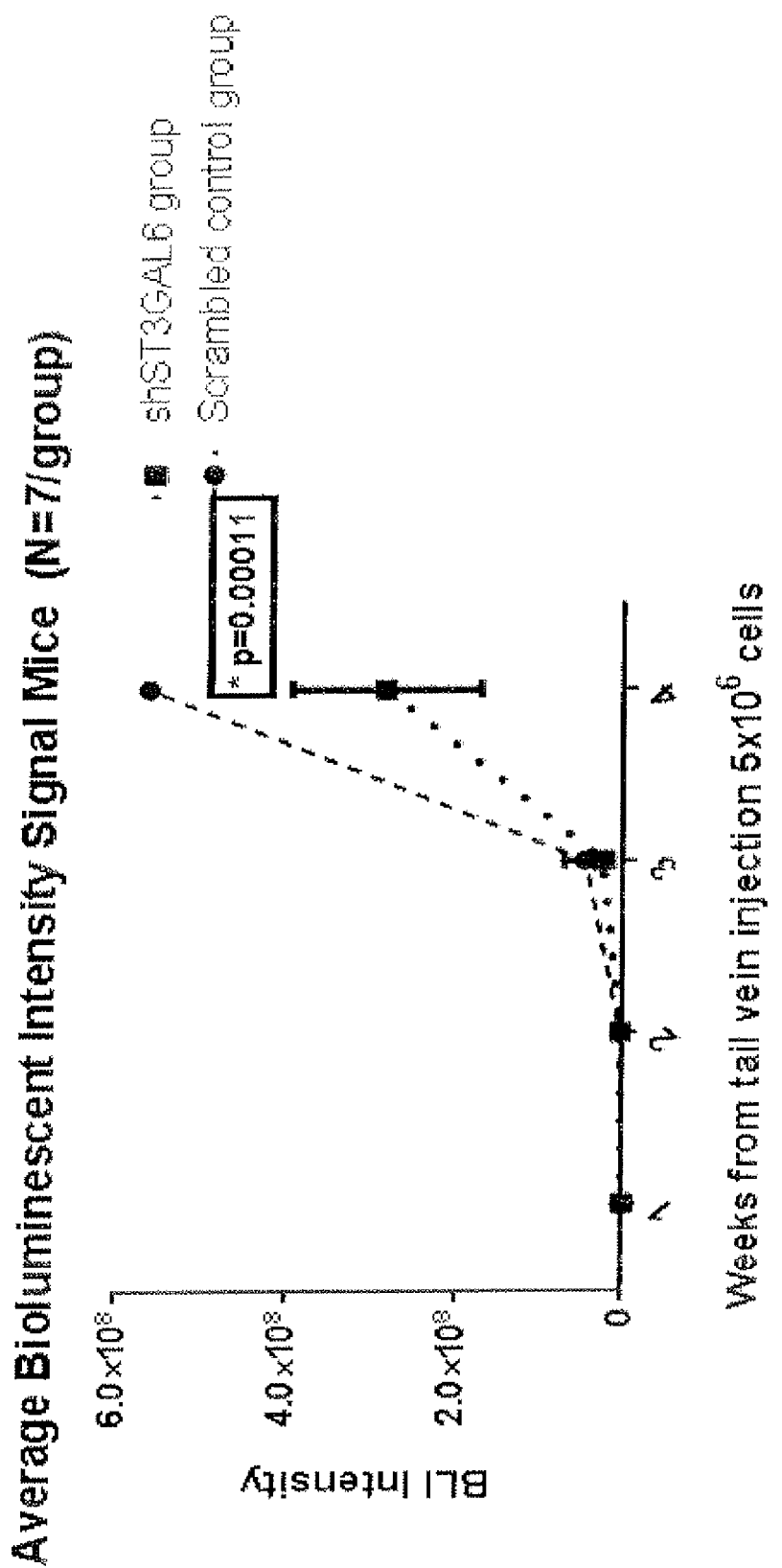
FIG. 13. Average bioluminescent intensity signal in SCID-Bg mice (N=7/group).
Figure 14:
FIGS. 14A and 14B. In-vivo confocal imaging performed in SDID-Bg xenograft mice skull bones. Red represents vessels stained with Evans Blue dye, green represents myeloma cells (MM1s-GFP+ cell line, (n=3/group, representative images shown from two mice).
Figure 14:
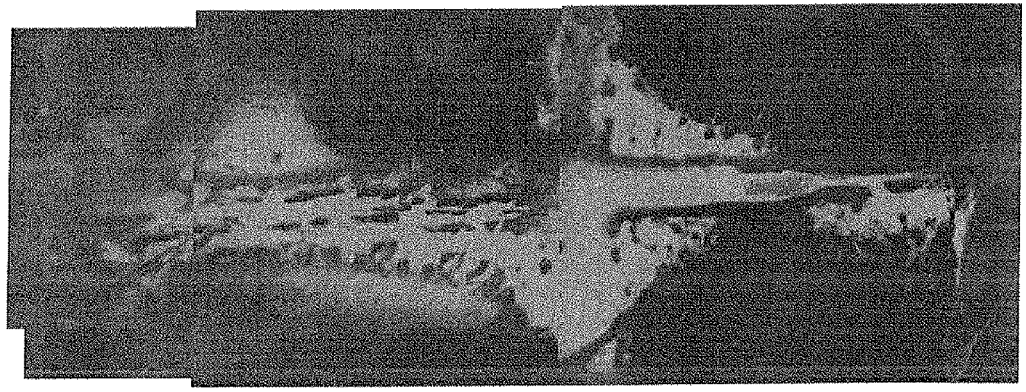

In-vivo studies in the SCID-bg xenograft mouse model of MM were conducted to assess the effect of shST3GAL6 on myeloma xenograft tumour growth in-vivo compared with scrambled control cells were conducted. FIG. 13 shows bioluminescent imaging of SCID-Bg mice weeks 1-4 post 1×10$^6$ MM1s-GFP-Luc positive cells/mouse injected IV via tail vein. Scrambled control group received cells that were infected with a standard scrambled control lentivirus (shGFP). Animals were imaged each week for monitoring of tumour development 5 minutes post intraperitoneal injection of luciferase enzyme as per standard protocol. At week four animals were sacrificed for confocal imaging. In-vivo confocal imaging was performed on SDID-Bg xenograft mice skull bones. In FIGS. 14A and 14B red represents vessels stained with Evans Blue dye, green represents myeloma cells (MM1s-GFP+ cell line) and can be taken to represent tumour burden in the skull bone marrow. Images taken 4 weeks following injection of 5×10$^6$ cells injected intravenously via tail vein. Mouse A was injected with scrambled control cells, mouse B was injected with MM1 s-GFP+ cells that had been infected with shRNA for ST3GAL6 resulting in a stable knockdown of this gene in the cell line. A number of other glycosylation genes are differentially regulated between normal and malignant plasma cells in MM. The prognostic significance of certain genes was analysed using Kaplan Meier survival estimates for progression free survival and overall survival. Low expression (lower quartile by GEP) of the gene FUCA1, was linked to inferior outcome (median OS 44 .v. 38 mos, p=0.025). On multivariate analysis low FUCA1 expression was independent of other important prognostic factors. FUCA1 expression was not copy number sensitive and there was no correlation with methylation status in the MRCIX dataset.

MM cell lines show low levels of FUCA1 transcripts by QPCR. The OPM2 cell line, which contains t(4;14) showed increased ST3GAL1 transcripts relative to NBM. High expression (top quartile) of the sialytranserase gene ST3GAL1 also showed a trend towards inferior OS (median survival 35 mos .v. 45 mos, p=0.07) with significantly reduced PFS (19 .v. 14 mos, p=0.015). Increased expression of ST3GAL1 correlated with the presence of t(4;14) (p=0.009), del13q (p=0.001), +1q (p=0.01) and hypodiploidy (p=0.00001).

Figure 15:
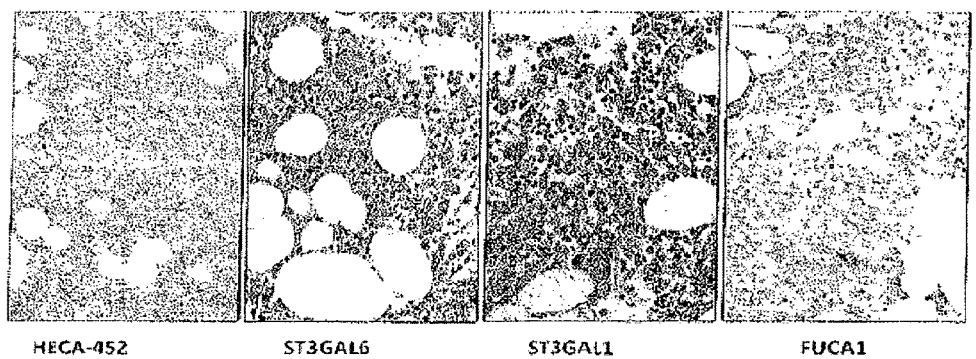
FIG. 15: Myeloma cells express sialytransferases and sLex.

As shown in FIG. 15 myeloma cells express sialytransferases and sLex/a. Since FUCA1 participates in N-glycan degradation with removal of fucose residues, this raises the possibility that a reduction in FUCA1 may lead to excessive fucosylation of cancer related glycans involved in adhesion and trafficking, such as sLex. Lectin arrays of MM cell lines revealed in high levels of a-1,3/a-1,6 linked fucose, as determined by binding of Aleuria *Aurantia* Lectin (AAL) (data not shown). The HECA-452 antibody recognizes a functional trisaccharide domain shared by sialyl Lewis a and sLex and known to bind to E-selectin. Preliminary immunohistochemistry revealed increased HECA452 staining (D) in bone marrow samples, which had both strong ST3GAL6 (A)+/ST3GAL (B) and low FUCA1 staining (C).

Figure 16:
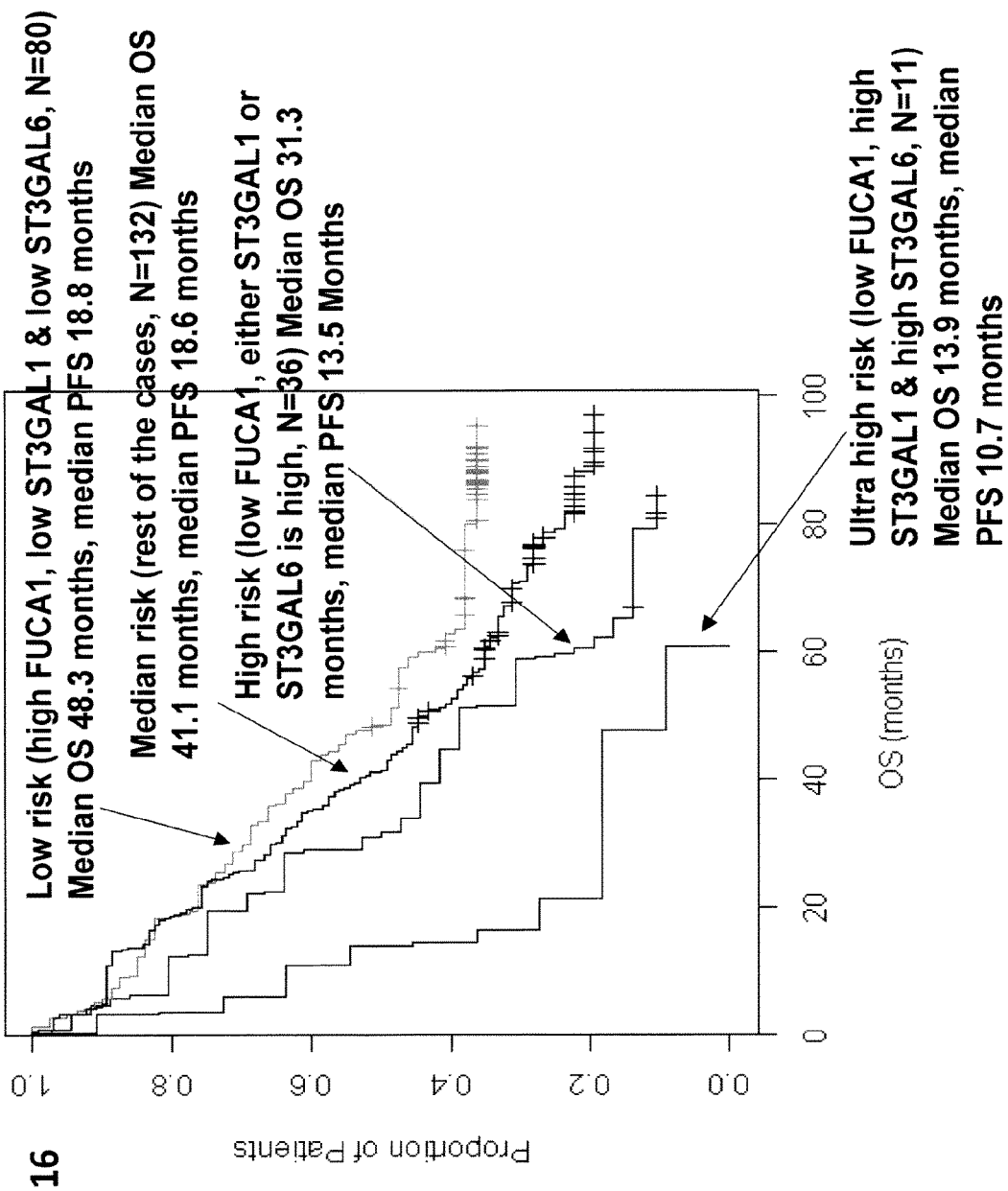
FIG. 16. Combining gene expression data of FUCA1 with expression of either ST3GAL6 or ST3GAL1 or both, patients with a particularly poor outcome are shown in red and black lines.

Combining gene expression data showed that reduced expression of FUCA1 with increased expression of either ST3GAL6 or ST3GAL1 or both, identified a subgroup of patents (18%) in MRC Myeloma IX with particularly poor outcome (red and black lines), as shown in FIG. 16. Similar results where found in independent datasets with 17% of patients affected.

CONCLUSIONS

The sialyltransferase ST3GAL6 is differentially regulated in all stages of MM with potential effects on MM biology and survival. Upregulation of ST3GAL6 may play an important role in MM cell trafficking and in this analysis is associated with inferior survival. Studies are ongoing to address the roles of ST3GAL6 over expression and altered sialylation in MM cell adhesion and trafficking.

The present inventors have shown that this glycogene is overexpressed in multiple myeloma cell lines and in CD138 cells from myeloma patients when compared to their healthy counterparts. We have also demonstrated an association between increased expression of this gene and reduced median survival following analysis of a publically available transcriptomic dataset.

Altered glycosylation gene expression patters may identify patients at high risk of disease progression and early death. Our data implicates sialytransferases and selectin ligands as potential therapeutic targets in Multiple Myeloma. In particular, low expression of the FUCA1 gene is an adverse prognostic factor in MM and when combined with high sislyltransferase gene expression identifies patients at increased risk of early disease progression and death.

REFERENCES

1. Alsayed, Y., et al., *Mechanisms of regulation of CXCR4/SDF-1 (CXCL12)-dependent migration and homing in multiple myeloma*. Blood, 2007, 109(7): p. 2708-17.
2. Hideshima, T., et al., *Molecular mechanisms mediating antimyeloma activity of proteasome inhibitor PS-341*. Blood, 2003, 101(4): p. 1530-4.
3. Roccaro, A. M., et al., *Bortezomib mediates antiangiogenesis in multiple myeloma via direct and indirect effects on endothelial cells*. Cancer Res, 2006, 66(1): p. 184-91.

4. Dillon, C. P., et al., *Rnai as an experimental and therapeutic tool to study and regulate physiological and disease processes.* Annu Rev Physiol, 2005, 67: p. 147-73.
5. Wang, Z., et al., *Roles for UDP-GlcNAc 2-epimerase/ManNAc 6-kinase outside of sialic acid biosynthesis: modulation of sialytransferase and BiP expression, GM3 and GD3 biosynthesis, proliferation, and apoplosis, and ERK1/2 phosphorylation.* J Biol Chem, 2006. 281(37): p. 27016-28.
6. Azab. A. K., et al., *CXCR4 inhibitor AMD3100 disrupts the interaction of multiple myeloma cells with the bone marrow microenvironment and enhances their sensitivity to therapy.* Blood, 2009. 113(18): p. 4341-51.
7. Leleu, X., et al., *The Akt pathway regulater survival and homing in Waldenstrom macroglobulinemia.* Blood, 2007. 110(13): p. 4417-26.
8. Roccaro, A. M., et al., *MicroRNAs 15a and 16 regulate tumor proliferation in multiple myeloma.* Blood, 2009. 113(26): p. 6669-80.
9. Azab, A. K., et al., *RhoA and Rac1 GTPfases play major and differential roles in stromal cell-derived factor-1-induced cell adhesion and chemotaxis in multiple myeloma.* Blood, 2009. 114(3): p. 619-29.

13 Nature, 2005 Jun. 16;435(7044):969-73. In vivo imaging of specialized bone marrow endothelial microdomains for tumour engraftment.

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A method of treating multiple myeloma in a subject in need thereof, the method comprising administering to the subject a modulator of ST3GAL6 in an amount sufficient to decrease ST3GAL6 expression or activity, wherein the modulator of ST3GAL6 is an interfering RNA specific for ST3GAL6.

2. The method of claim 1, wherein the interfering RNA is encoded by a nucleotide comprising the sequence set forth in SEQ ID No. 3 and/or SEQ ID No. 4.

\* \* \* \* \*

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: forward Primer

<400> SEQUENCE: 1
ttgcctctct gctgaggttt                                              20

<210> SEQ ID NO 2
<211> LENGTH: 20
<212> TYPE: DNA
<213> ORGANISM: Artificial Sequence
<220> FEATURE:
<223> OTHER INFORMATION: Reverse primer

<400> SEQUENCE: 2
cctccattac caaccaccac                                              20

<210> SEQ ID NO 3
<211> LENGTH: 21
<212> TYPE: DNA
<213> ORGANISM: Human

<400> SEQUENCE: 3
cctttgcact actatgggaa t                                            21

<210> SEQ ID NO 4
<211> LENGTH: 21
<212> TYPE: DNA
<213> ORGANISM: Human

<400> SEQUENCE: 4
ccagccttaa acctgattta t                                            21
```